US008524198B2

(12) United States Patent
Bailey

(10) Patent No.: US 8,524,198 B2
(45) Date of Patent: Sep. 3, 2013

(54) XYLITOL DENTAL MAINTENANCE SYSTEM

(76) Inventor: Donald W. Bailey, Provo, UT (US)

(*) Notice: Subject to any disclaimer, the term of this patent is extended or adjusted under 35 U.S.C. 154(b) by 1442 days.

(21) Appl. No.: 10/873,766

(22) Filed: Jun. 21, 2004

(65) Prior Publication Data
US 2005/0025720 A1 Feb. 3, 2005

Related U.S. Application Data

(60) Provisional application No. 60/480,516, filed on Jun. 20, 2003.

(51) Int. Cl.
A61K 8/00 (2006.01)
A61K 9/68 (2006.01)
A61C 17/28 (2006.01)

(52) U.S. Cl.
USPC ............ 424/49; 424/440; 424/48; 433/216

(58) Field of Classification Search
USPC ................... 424/48, 49, 440; 433/216
See application file for complete search history.

(56) References Cited

U.S. PATENT DOCUMENTS

| | | | |
|---|---|---|---|
| 3,970,747 A | 7/1976 | Barth | |
| 4,148,872 A | 4/1979 | Wagenknecht et al. | |
| 4,150,112 A | 4/1979 | Wagenknecht et al. | |
| 4,156,715 A | 5/1979 | Wagenknecht et al. | |
| 4,156,716 A | 5/1979 | Wagenknecht et al. | |
| 4,157,385 A | 6/1979 | Wagenknecht et al. | |
| 4,159,315 A | 6/1979 | Wagenknecht et al. | |
| 4,160,054 A | 7/1979 | Wagenknecht et al. | |
| 4,160,820 A | 7/1979 | Wagenknecht et al. | |
| 4,161,517 A | 7/1979 | Wagenknecht et al. | |
| 4,170,632 A | 10/1979 | Wagenknecht et al. | |
| 4,170,633 A | 10/1979 | Wagenknecht et al. | |
| 4,238,475 A | 12/1980 | Witzel et al. | |
| 4,254,101 A | 3/1981 | Denny, Jr. | |
| 4,302,441 A | 11/1981 | Mühlemann et al. | |
| 4,314,990 A | 2/1982 | Denny, Jr. et al. | |
| 4,340,583 A | 7/1982 | Wason | |
| 4,556,553 A | 12/1985 | Suganuma et al. | |
| 4,568,537 A | 2/1986 | Hoerman et al. | |
| 4,581,228 A | 4/1986 | Suganuma et al. | |
| 4,645,662 A | 2/1987 | Nakashima et al. | |
| 4,693,888 A | 9/1987 | Miyahara et al. | |
| 4,726,943 A | 2/1988 | Klueppel et al. | |
| 4,795,630 A | 1/1989 | Okouchi et al. | |
| 4,822,597 A | 4/1989 | Faust et al. | |
| 4,828,845 A | 5/1989 | Zamudio-Tena et al. | |
| 4,853,212 A | 8/1989 | Faust et al. | |
| 4,867,989 A | 9/1989 | Silva et al. | |
| 4,906,455 A | 3/1990 | Hoerman | |
| 4,911,934 A | 3/1990 | Yang et al. | |
| 4,931,294 A | 6/1990 | Yatka et al. | |
| 4,976,954 A | 12/1990 | Kleber et al. | |
| 4,976,972 A | 12/1990 | Patel et al. | |
| 4,986,991 A | 1/1991 | Yatka et al. | |
| 4,997,654 A | 3/1991 | Corsello et al. | |
| 5,013,541 A | 5/1991 | Elliott et al. | |
| 5,017,400 A | 5/1991 | Olinger et al. | |
| 5,034,214 A | 7/1991 | Palmer et al. | |
| 5,041,294 A | 8/1991 | Patel | |
| 5,045,340 A | 9/1991 | Kohler | |
| 5,064,640 A | 11/1991 | Kleber et al. | |
| 5,089,255 A | 2/1992 | Gaffar et al. | |
| 5,248,508 A | 9/1993 | Reed et al. | |
| 5,256,402 A | 10/1993 | Prencipe et al. | |
| 5,258,199 A | 11/1993 | Moore et al. | |
| 5,270,061 A | 12/1993 | Reed et al. | |
| 5,370,881 A | 12/1994 | Fuisz | |
| 5,376,360 A | 12/1994 | Domke et al. | |
| 5,441,749 A | 8/1995 | Meyers et al. | |
| 5,470,566 A | 11/1995 | Lützen | |
| 5,496,541 A | 3/1996 | Cutler | |
| 5,560,906 A * | 10/1996 | Scodari et al. | 424/54 |
| 5,618,517 A | 4/1997 | Miskewitz | |
| 5,624,906 A * | 4/1997 | Vermeer | 514/23 |
| 5,629,035 A | 5/1997 | Miskewitz | |
| 5,679,389 A | 10/1997 | Wong et al. | |
| 5,693,334 A | 12/1997 | Miskewitz | |
| 5,698,215 A | 12/1997 | Kalili et al. | |
| 5,702,687 A | 12/1997 | Miskewitz | |
| 5,824,291 A * | 10/1998 | Howard | 424/48 |
| 5,869,029 A | 2/1999 | Graff-Andersen et al. | |
| 5,885,553 A | 3/1999 | Michael | |
| 5,900,230 A | 5/1999 | Cutler | |
| 5,952,019 A | 9/1999 | Yatka et al. | |
| 6,042,812 A | 3/2000 | Sanker et al. | |
| 6,054,119 A | 4/2000 | Hurme et al. | |
| 6,083,527 A | 7/2000 | Thistle | |
| 6,086,856 A * | 7/2000 | Saferstein et al. | 424/58 |
| 6,180,143 B1 | 1/2001 | Rapp et al. | |
| 6,190,705 B1 | 2/2001 | Richey | |
| 6,207,138 B1 * | 3/2001 | Zhang et al. | 424/49 |

(Continued)

OTHER PUBLICATIONS

Xylitol.org, http://www.xylitol.org, pp. 1-5, Feb. 2001.*

Primary Examiner — Lezah Roberts
Assistant Examiner — Tracy Liu
(74) Attorney, Agent, or Firm — Terrence J. Edwards; TechLaw Ventures, PLLC

(57) ABSTRACT

A kit for promoting oral hygiene, and a method for using such a kit are disclosed. The kit may comprise several compositions or a single composition, each of which comprises an effective amount of xylitol. For example, the kit may comprise a chewing gum composition, a morsel composition, a paste-like composition, and an oral rinse composition; or any one of the above compositions; or any combination thereof. It will be appreciated that a novel method for using such a kit for promoting oral hygiene may include: brushing a user's teeth with the paste-like composition comprising at least about 0.05 g to about 0.75 g of xylitol at least in the morning and in the evening, administering at least about 0.75 g of xylitol after consumption of nutrition by chewing a gum composition or by partaking of a morsel composition, and rinsing the user's oral cavity with an oral rinse composition comprising at least about 0.75 g of xylitol at least before bedtime.

1 Claim, 5 Drawing Sheets

(56) References Cited

U.S. PATENT DOCUMENTS

| | | |
|---|---|---|
| 6,235,318 B1 | 5/2001 | Lombardy, Jr. et al. |
| 6,238,690 B1 | 5/2001 | Kiefer et al. |
| 6,290,985 B2 | 9/2001 | Ream et al. |
| 6,322,806 B1 | 11/2001 | Ream et al. |
| 6,344,222 B1 | 2/2002 | Cherukuri et al. |
| 6,350,437 B1 | 2/2002 | Pasetti et al. |
| 6,355,265 B1 | 3/2002 | Ream et al. |
| 6,416,744 B1 | 7/2002 | Robinson et al. |
| 6,432,388 B1 | 8/2002 | Alvarez Hernandez |
| 6,440,394 B2 | 8/2002 | Barth et al. |
| 6,444,241 B1 | 9/2002 | Tyrpin et al. |
| 6,482,395 B1 | 11/2002 | Barth et al. |
| 6,485,710 B2 | 11/2002 | Zuckerman |
| 6,534,527 B2 | 3/2003 | Wolfson et al. |
| 6,541,048 B2 | 4/2003 | Zyck et al. |
| 6,558,692 B2 | 5/2003 | Ream et al. |
| 2001/0009660 A1 | 7/2001 | Delli Santi et al. |
| 2001/0021373 A1 | 9/2001 | Zyck et al. |
| 2001/0024642 A1 | 9/2001 | Ream et al. |
| 2001/0036468 A1 | 11/2001 | Han et al. |
| 2002/0039560 A1 | 4/2002 | Ream et al. |
| 2002/0064506 A1 | 5/2002 | Pellicano et al. |
| 2002/0076384 A1 | 6/2002 | Orlowski et al. |
| 2002/0081270 A1 | 6/2002 | Delli Santi et al. |
| 2002/0114767 A1 | 8/2002 | Rolla |
| 2002/0127189 A1 | 9/2002 | Myers et al. |
| 2002/0159956 A1 | 10/2002 | Ream et al. |
| 2002/0187108 A1 | 12/2002 | Rajaiah et al. |
| 2002/0197215 A1 | 12/2002 | Stier |
| 2003/0003059 A1 | 1/2003 | Dana |
| 2003/0007937 A1 | 1/2003 | Lawlor |
| 2003/0007997 A1 | 1/2003 | Lawlor |
| 2003/0012745 A1 | 1/2003 | Dana et al. |
| 2003/0026826 A1 | 2/2003 | Cherukuri et al. |
| 2003/0059501 A1 | 3/2003 | Rivier |
| 2003/0068422 A1 | 4/2003 | Rivier |
| 2003/0082113 A1 | 5/2003 | Rajaiah et al. |
| 2003/0091514 A1 | 5/2003 | Stier |

\* cited by examiner

XYLITOL DENTAL MAINTENANCE SYSTEM

CROSS-REFERENCE TO RELATED APPLICATIONS

This application claims the benefit of U.S. Provisional Application No. 60/480,516, filed Jun. 20, 2003, entitled "XYLITOL DENTAL MAINTENANCE SYSTEM," which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said portion of said above-referenced provisional application.

STATEMENT REGARDING FEDERALLY SPONSORED RESEARCH OR DEVELOPMENT

Not Applicable.

BACKGROUND

1. The Field of the Invention

The present disclosure relates generally to oral care compositions and methods of use, and more particularly, but not necessarily entirely, to a dental maintenance system that integrates multiple cavity protecting products into an integrated and easily implemented oral hygiene kit and system.

2. Description of Related Art

Dental caries is an ecological disease in which the diet, the host and the microbial flora interact over a period of time in such a way as to encourage demineralization of the tooth enamel with resultant caries formation. Dental caries is one of the most common diseases in the world today, and until recently almost everyone in the world had experienced tooth decay in their lifetime. However, today many people are caries free and there has been a forty to sixty percent (40-60%) reduction in the incidence of tooth decay within the Western world. Most developed countries and many non-industrialized countries are now well below the World Health Organization's goal of less than three decayed, missing or filled teeth per twelve-year old child.

Teeth are composed of a thin layer (1-2 mm) of dental enamel, which forms the hard protective coating over each tooth. Teeth consist mainly of calcium, phosphate and other ions in a structure known as "hydroxyapatite." Dental enamel is porous and is susceptible to acid dissolution during the process of demineralization. This demineralization process is offset by the repair process known as remineralization. Tooth susceptibility to dental caries varies among individuals. Although the reasons for the variation are not fully known, some influences include: (a) the shape, size and order of the teeth that affect the "washing" effects of saliva, which is largely determined by hereditary factors; (b) salivary components which can be critical in controlling dental caries since salivary components affect bacteria, immune status, plaque formation, and enamel structure and can neutralize acids, and therefore saliva has a vital role in the balance between demineralization and remineralization; and (c) enamel structure can be altered by a selection of mineral ions and fluoride, as well as by acid, and the balance between demineralization and remineralization of the enamel determines whether caries will occur.

However, fluoride is toxic. Fluoride's toxic impacts are cumulative, meaning that only fifty percent (50%) of ingested fluoride is excreted through the kidneys, while the remainder accumulates in the body. Fluoride is effective only in its topical application, and not in its systemic application. Humans can have perfectly good teeth without fluoride, as fluoride is not an essential nutrient. It will be appreciated that fluoride may lead to a condition known as dental fluorosis, which is the incomplete development of the dental enamel and is characterized by defective calcification that mottles teeth. Fluoride has been shown to be mutagenic, to cause chromosome damage, and to interfere with enzymes involved in DNA repair. Additionally, fluoride facilitates the uptake of certain damaging metals into the body. Studies have suggested that fluoride can exacerbate certain neurological defects. Fluoride can also interfere with the function of the thyroid gland. Fluoride can also lead to skeletal fluorosis, which mimics the symptoms of arthritis. Therefore, the risks associated with ingested fluoride far outweigh the benefits.

Dental caries, or cavities, are bacterial infections that cause the tooth structure to deteriorate. The compositions disclosed herein fight cavities from their novel use of xylitol in several integrated products. Xylitol is a clinically proven cariostatic sweetener that reduces the ability of cavity-causing bacteria to impact oral health. Because of xylitol's cariostatic attributes, cavities cannot form in its presence. As such, it is a valuable tool in preventing and fighting cavities. While the United States Food and Drug Administration has not approved cavity prevention claims for xylitol, several studies substantiate its efficacy. Some studies even suggest that xylitol may aid in the reversal of certain types of cavities.

The international community has performed most of these studies regarding xylitol's efficacy. Only recently, has the United States dental community begun to embrace xylitol as an effective tool in caries management therapy.

Although more than forty (40) studies demonstrate the impact of xylitol on cavities, two of the most illustrative are highlighted below. Studies such as these lay a strong scientific foundation for the product efficacy assertions of xylitol.

The first study was a 40-month double-blind cohort study of 1,135 school children used to determine the impact of sugar-free gums on the incidences of cavities. As illustrated in FIG. 1, the study reviewed the change in decayed, missing, and/or filled surfaces (DMFS) of subjects in several groups. The group that chewed xylitol gum actually had a reduction in DMFS, while all other groups including no gum, sugar gum, and sugar-free gum saw substantial increases in DMFS. The researchers concluded, a "xylitol-based chewing gum program in basic caries prevention can be substantial." Makinen K K, Bennett C A, Hujoel P P, Isokangas P J, Isotupa K P, Pape H R Jr, Makinen K K. *Xylitol chewing gums and caries rates: a 40-month cohort study.* J Dent Res December 1995; 74(12): 1904-13.

The second study was a 24-month double-blind study of more than 500 six-year old children used to determine the effect of xylitol on the rehardening of dentine lesions in the primary dentition. As illustrated in FIG. 2, researchers administered xylitol gum, sugar-free gum and no gum to participants who had small cavities. The subjects' cavities were then evaluated to determine if the carious lesions had been rehardened. The researchers found "that high-xylitol content chewing gum usage can retard or arrest rampant dentine caries." Makinen K K, Hujoel P P, Bennett C A, Isotupa K P, Makinen P L, Allen P. *Polyol chewing gums and caries rates in primary dentition: a 24-month cohort study.* Caries Res 1996; 30(6): 408-17.

The scientific evidence supporting xylitol's dental benefits provides a solid foundation that xylitol products substantially reduce cavities without the use of fluoride. Because xylitol can be used as a direct substitute for sugar, its dental benefits can be derived through a variety of product applications.

There are several xylitol containing compositions known in the art, such as that disclosed in U.S. Pat. No. 5,496,541 (granted Mar. 5, 1996 to Cutler). This reference discloses several dental products employing a ternary surfactant system of poloxamers, anionic polysaccharides, and nonionic cellulose ethers. This reference also includes a mild abrasive plus one or more of the following: xylitol, raw licorice, licorice extract, and glycyrrhizin and its derivatives. This reference also discloses dental products that may comprise fluoride, which is disadvantageous when used in gum, mints, toothpaste, mouthwash, and other dental products that may be ingested because fluoride is toxic and accumulates in the body.

Another xylitol containing composition is disclosed in U.S. Pat. No. 5,900,230 (granted May 4, 1999 to Cutler). This reference discloses several dental products that can be used to treat and prevent periodontal disease. These products contain a mixture of poloxamers, and/or poloxamer congeners, plus xylitol. This reference also teaches dental products that may comprise fluoride, which is disadvantageous when used in gum, mints, toothpaste, mouthwash, and other dental products that may be ingested because fluoride is toxic and accumulates in the body.

U.S. patent Publication No. 2003/0091514 (published May 15, 2003 to Stier) discloses several oral care compositions comprising diglycerol in addition to various other ingredients for flavoring, sweetening, thickening and the like. Similar to the above mentioned references, this reference discloses dental products that may comprise fluoride, which is disadvantageous when used in gum, mints, toothpaste, mouthwash, and other dental products that may be ingested because fluoride is toxic and accumulates in the body.

It is noteworthy that none of the prior art known to applicant provides an effective amount of xylitol used in fluoride-free dental products for promoting oral hygiene as disclosed in detail below. There is a long felt, but unmet, need for such products in the market today that are relatively inexpensive to produce and manufacture, and are therefore readily available to the general public.

The art is thus characterized by several disadvantages that are addressed by the compositions disclosed herein. The present compositions of the present disclosure minimizes, and in some aspects eliminates, the above-mentioned failures, and other problems, by utilizing the methods and compositions described herein.

The features and advantages of the disclosure will be set forth in the description which follows, and in part will be apparent from the description, or may be learned by the practice of the disclosure without undue experimentation. The features and advantages of the disclosure may be realized and obtained by means of the compositions and combinations particularly pointed out herein.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
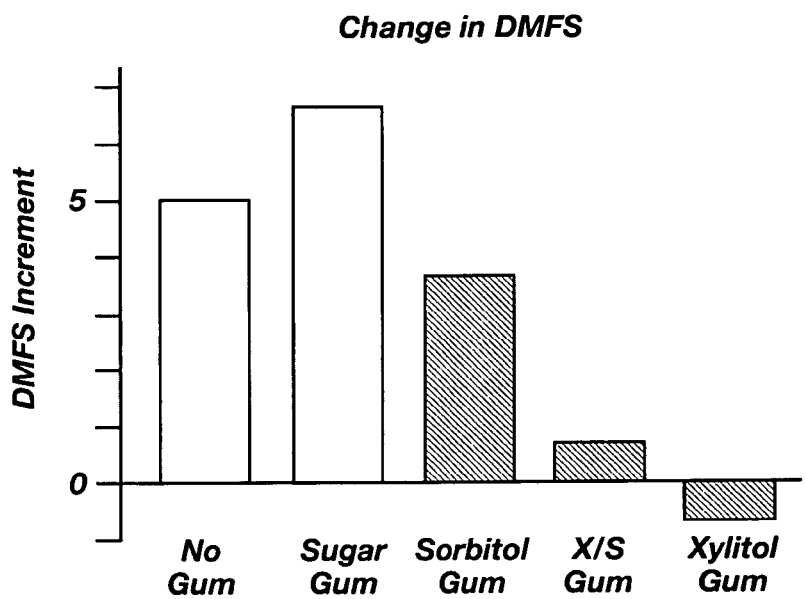
FIG. 1 is a chart illustrating the change in decayed, missing, and/or filled surfaces (DMFS) of subjects in several groups.
Figure 2:
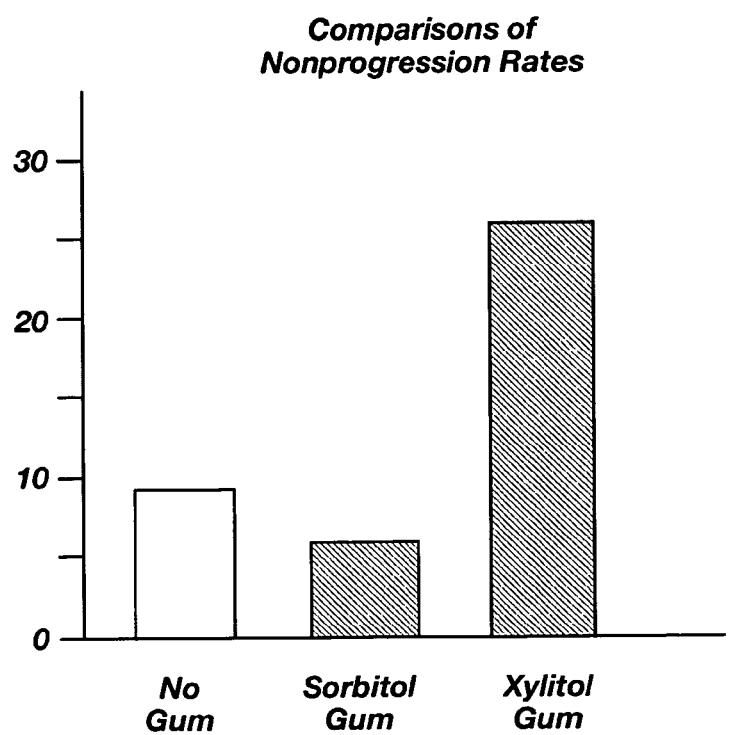
FIG. 2 is a chart illustrating the effect of xylitol on the rehardening of dentine lesions in the primary dentition.

For the purposes of promoting an understanding of the principles in accordance with the present disclosure, reference will now be made to the embodiments and examples of the present disclosure, and specific language will be used to describe the same. It will nevertheless be understood that no limitation of the scope of the disclosure is thereby intended. Any alterations and further modifications of the inventive features contained herein, and any additional applications of the principles of the disclosure as described herein, which would normally occur to one skilled in the relevant art and having possession of this disclosure, are to be considered within the scope of the disclosure claimed.

Before the present compositions and methods for promoting oral hygiene are disclosed and described, it is to be understood that this disclosure is not limited to the particular compositions, configurations, process steps, ingredients and materials disclosed herein as such configurations, process steps, and materials may vary somewhat. It is also to be understood that the terminology employed herein is used for the purpose of describing particular embodiments only and is not intended to be limiting since the scope of the present disclosure will be limited only by the appended claims and equivalents thereof.

The publications and other reference materials referred to herein to describe the background of the disclosure, and to provide additional detail regarding the practice of using xylitol, are hereby incorporated by reference herein in their entireties, with the following exception: In the event that any portion of said reference materials is inconsistent with this application, this application supercedes said reference materials. The reference materials discussed herein are provided solely for their disclosure prior to the filing date of the present application. Nothing herein is to be construed as a suggestion or admission that the inventors are not entitled to antedate such disclosure by virtue of prior invention, or to distinguish the present disclosure from the subject matter disclosed in the reference materials.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, an "effective amount" is an amount sufficient to effect beneficial or desired results. An effective amount can be administered in one or more administrations, applications or dosages. For example, an effective amount of xylitol is an amount sufficient to reduce dental plaque, suppress bacterial growth, and reduce adhesiveness of plaque, to thereby inhibit formation of dental caries. Such effective amounts can be determined without undue experimentation by those skilled in the art.

Applicant has discovered that maintaining and promoting oral hygiene may be greatly enhanced by utilizing a unique kit having a combination of various dental compositions. Applicant has thus conceived of an oral hygiene kit capable of reducing dental plaque, suppressing bacterial growth, and reducing adhesiveness of plaque to thereby inhibit formation of dental caries.

It will be appreciated that fluoride is toxic to humans, and fluoride's toxic impacts are cumulative. Specifically, only about 50% of ingested fluoride is excreted through the kidneys, while the remainder accumulates in the human body. Fluoride is effective only in its topical application, but is not effective in its systemic application. Accordingly, humans can have healthy teeth and gums without the use of fluoride, as fluoride is not an essential nutrient. Due to its accumulative effects, fluoride may lead to dental fluorosis, which is the incomplete development of the dental enamel characterized by defective calcification that mottles teeth. Fluoride has also been shown to be mutagenic, to cause chromosome damage, and to interfere with enzymes involved in DNA repair.

Additionally, fluoride may facilitate the uptake of certain damaging metals into the body. Studies have even suggested that fluoride can exacerbate certain neurological defects. Further, fluoride can interfere with the function of the thyroid gland, and can lead to skeletal fluorosis, which mimics the symptoms of arthritis. Accordingly, the risks associated with ingested fluoride far outweigh the benefits. Therefore, applicant has developed several unique fluoride-free products and a regimen for using those products to maintain and promote oral health. Therefore, oral hygiene may be maintained and promoted without the use of fluoride in the compositions of the present disclosure.

Cavities are bacterial infections that cause the tooth structure to deteriorate and decay. The present disclosure fights cavities using xylitol in several products and compositions explained in more detail below. Xylitol itself is a clinically proven cariostatic sweetener that reduces the ability of cavity-causing bacteria to impact oral health. Because of xylitol's cariostatic attributes, cavities cannot form in its presence. As such, it is a valuable tool in preventing and fighting cavities.

Strategies for treating dental caries have been varied in the past, but it is understood that to maintain good oral hygiene and reduce the occurrence of dental caries, oral *mutans streptococci*, or MS, must be suppressed. Using only a mouthwash, for example a mouthwash containing chlorhexidine, will inhibit MS levels for a short period of time, but oral MS levels tend to quickly return to baseline values without further intervention. It has been found that the regular use of products and compositions containing xylitol over a sustained period of time will further reduce the occurrence of dental caries by reducing MS levels.

According to Birkhed, D. in an article entitled "Cariologic aspects of xylitol and its use in chewing gum: a review," found in Acta Odontol Scand 1994 April; 52(2):116-27, several studies have indicated that xylitol is not metabolized into acids either in pure cultures of oral microorganisms in vitro or in dental plaque in vivo. Consequently, persistent consumption of xylitol-sweetened chewing gum has resulted in reduction of dental plaque, suppression of *mutans streptococci*, and reduced adhesiveness of plaque. It has been demonstrated that a daily intake of two to three pieces of a xylitol chewing gum composition may result in a reduction of dental caries. Additionally, there are indications that regular and prolonged use of xylitol chewing gum may have a caries-preventive effect.

Additionally, several studies have resulted in further support of the use of xylitol as an effective way to treat DMFS as compared to fluoride. Xylitol has performed as well as or better than fluoride in side-by-side trials, as evidenced by the studies below.

A study by Scheinin A, Pienihakkinen K, Tiekso J, Banoczy J, Szoke J, Esztari I, Zimmermann P, Hadas E. entitled "Collaborative WHO xylitol field studies in Hungary. VII. Two-year caries incidence in 976 institutionalized children" and reported in Acta Odontol Scand. December 1985; 43(6): 381-7, assessed caries increment as influenced by partial substitution of sucrose by xylitol (X group) over a 2-year period in comparison with systemic fluoride (F group) and restorative treatment only © group). The study consisted of 976 children (ages 6-12 years old). The 2-year DMFS increment was 3.8 in the X group, 4.8 in the F group, and 6.0 in the C group. The corresponding ratio (RS) between caries incidence and the tooth surface population at risk was RSX, 4.5; RSF, 5.5; and RSC, 7.5. The xylitol regimen was shown to result in a lower increment of caries than measured in the F and C groups. Accordingly, xylitol was shown to be an effective alternative to fluoride in treating DMFS.

Another study by Szoke J, Pienihakkinen K, Esztari I, Banoczy J, Scheinin A, entitled "Collaborative WHO xylitol field studies in Hungary. V. Three-year development of oral hygiene" and reported in Acta Odontol Scand. December 1985; 43(6):371-6, illustrated the efficacy of xylitol in treating DMFS. In this study, the oral hygiene conditions were evaluated within a 3-year field study aimed at assessing the cariostatic value of partial substitution of sucrose by xylitol (X group) in comparison with systemic fluoride (F group) and restorative treatment only © group). The observations were analyzed with regard to sex, age, experimental grouping, and total development. The oral hygiene conditions of the subjects were generally poor, and at the base-line examination only 26% of the children had acceptable oral hygiene. However, at the end of the study this level was increased by 16% and reached 42%. A definite improvement was measured only in the X group, in which the final values differed significantly (p less than 0.001) from the base-line values and also from the end situation in the F and C groups. It was thereby concluded and shown that the development was influenced by several factors, such as different snacking habits and access to sweets, the study per se, and xylitol-induced effects. Accordingly, xylitol was shown to be an effective alternative to fluoride in treating DMFS.

Still, xylitol can enhance the benefits of all prevention methods. Xylitol has been shown to be complementary with brushing, flossing, sealants, fluoride, and the antimicrobial rinse chlorhexidine. It should be noted that while high concentrations of fluoride can be damaging to humans because of its cumulative effects, lower concentrations of fluoride and chlorhexidine can be effective when teamed with xylitol.

The present disclosure is specifically designed to provide dental protection at the moments patients need it most. Specifically, the present disclosure provides patients with protection when bacteria that causes cavities and tooth decay are most likely to be active, i.e. after meals and snacks.

The present disclosure is directed to maintaining and promoting oral hygiene through the use of products and compositions containing xylitol. It will be appreciated that xylitol has a 5-carbon chemical structure that advantageously is not recognized by oral bacteria, including *mutans streptococci*. Additionally, xylitol is not fermented and, therefore, it will not result in acid production in plaque, and the pH levels in the mouth will remain neutral. Xylitol can also have the added benefit of actually reversing the fall of pH levels in the mouth (produced, for example, by sucrose) when, for instance, a person chews a xylitol-sweetened sugarless gum product. The oral pH is raised to a safe level, saliva flow is stimulated, which in turn helps to rinse away excess sucrose residues, and neutralizes any acids that have been formed.

Another benefit of xylitol is that saliva contains the minerals, in particular calcium and phosphate, which help to promote the remineralization of early cavities. The most fundamental difference between xylitol and other sweeteners is that xylitol reduces the amount of plaque and the virulence of *mutans streptococci* in plaque. Xylitol functions as a modulator of the oral flora, and when consumed regularly xylitol can even help to repair teeth by stimulating the remineralization of teeth already affected by cavities. Further, no matter how long xylitol is consumed (even during long term habitual use), oral bacteria will not adapt to metabolize xylitol, so the benefits of xylitol continue while it is being consumed, and has even been proved to continue after xylitol is no longer a part of daily use.

One illustrative embodiment of the present disclosure may comprise a kit for promoting oral hygiene, and it will be appreciated that the kit of the present disclosure may comprise one individual product or composition, or the kit may comprise several products or compositions. For example, the present disclosure may include a chewing gum composition only, or may include a combination of products or compositions, such as the chewing gum composition, a morsel composition, a paste-like composition, and an oral rinse composition. For exemplary purposes only and to streamline the present disclosure, each of the products or compositions will be discussed below as being part of the kit. However, as mentioned above, the kit may comprise more or less products or compositions than the stated below.

The kit of the present disclosure may include a chewing gum composition that may be chewed anytime, and particularly after meals and snacks. It will be appreciated that the chewing gum composition may be used as part of the kit or the chewing gum composition may be used alone, as an individually packaged product, without departing from the scope of the present disclosure.

The chewing gum composition of the present disclosure may be sweetened 100% by xylitol. The chewing gum composition may comprise an effective amount of xylitol by weight, and may further comprise gum base, at least one flavoring agent, glycerin, soy lecithin, gum arabic, titanium dioxide, carnauba wax, and resinous glaze. The chewing gum composition of the present disclosure may be characterized by the absence of fluoride. However, it will be appreciated that the composition of the chewing gum may be modified to include, or may be used in conjunction with, fluoride without departing from the scope of the present disclosure.

It will be appreciated that the amount of xylitol present in the chewing gum composition may be in a range from about 20% to about 85%, by weight, and more specifically in a range from about 25% to about 75%, by weight. Applicant has found that an advantageous amount of xylitol present in the chewing gum composition may be in a range from about 30% to about 70% by weight. Additional ranges that may supply a desired amount of xylitol may include a range from about 50% to about 85% by weight; or a range from about 60% to about 75% by weight; or a range from about 65% to about 70% by weight. Other possible ranges that may supply a desired amount of xylitol may also include a range from about 20% to about 50% by weight; or a range from about 25% to about 40% by weight; or a range from about 30% to about 35% by weight. It will be appreciated that any amount of xylitol may be present in the chewing gum composition in the ranges provided above, without departing from the spirit or scope of the present disclosure.

It will be appreciated that the amount of xylitol present in the chewing gum composition may be modified depending upon the desired amount of xylitol to be administered to a user. For example, a directly compressible gum application may be used, and may be comprised of a greater amount of xylitol than a traditional chewing gum piece. In any event, applicant has found that administering at least about 0.75 g of xylitol per dose to a user through chewing the gum composition of the present disclosure may be advantageous and may be expected to reduce MS levels, reduce dental plaque, suppress bacterial growth, and tends to reduce adhesiveness of plaque to thereby inhibit formation of, and reduce the incidence of, dental caries. Illustratively, chewing the xylitol gum composition for at least five minutes after meals and snacks, when bacteria that causes dental caries is most active, is expected to be advantageous for reducing MS levels and for maintaining and promoting oral health.

EXAMPLE 1

Xylitol Chewing Gun Composition

| Xylitol Chewing Gum Ingredients: | |
|---|---|
| xylitol | 0.89 g |
| gum base | 0.32 g |
| natural flavors | 0.025 g |
| glycerin | less than 0.01 g |
| gum arabic | 0.01 g |
| tapioca dextrin | less than 0.01 g |
| soy lecithin | 0.02 g |
| titanium dioxide | 0.01 g |
| carnauba wax | 0.01 g |
| confectioners glaze | less than 0.01 g |

In the case of the exemplary Xylitol Chewing Gum of Example 1, the ingredients can be provided in the following proportions: xylitol—greater than about 60%; gum base greater than about 20%; natural flavors—less than about 2%; glycerin, gum arabic, and tapioca dextrin—less than about 1% each; lecithin—less than about 2%; and titanium dioxide, carnauba wax, and confectioner's glaze—less than about 1% each.

Another composition that may be present in the kit of the present disclosure may be a morsel composition, such as mints, lozenges, or candies that may be consumed anytime, and particularly after meals and snacks. It will be appreciated that the morsel composition may be used as part of the kit or the morsel composition may be used alone, as an individually packaged product, without departing from the scope of the present disclosure.

The morsel composition, such as mints, lozenges, or candies, may be sweetened 100% by xylitol. The morsel composition of the present disclosure may further comprise an effective amount of xylitol, natural flavors, and calcium stearate. The morsel composition of the present disclosure may be characterized by the absence of fluoride. However, it will be appreciated that the composition of the morsel may be modified to include, or may be used in conjunction with, fluoride without departing from the scope of the present disclosure.

The amount of xylitol present in the morsel composition may be in a range from about 40% to about 100%, by weight. More specifically, the amount of xylitol present in the morsel composition may be in a range from about 50% to about 99%, by weight. For example, applicant has found that an advantageous amount of xylitol present in the morsel composition to be about 96% to about 98%, by weight. Additional ranges that may supply a desired amount of xylitol may include a range from about 75% to about 100% by weight; or a range from about 80% to about 99% by weight; or a range from about 85% to about 98% by weight; or a range from about 90% to about 96% by weight. Other possible ranges that may supply a desired amount of xylitol may also include a range from about 40% to about 75% by weight; or a range from about 50% to about 70% by weight; or a range from about 60% to about 65% by weight. It will be appreciated that the amount of xylitol present will likely depend upon the size of the morsel composition. It will be appreciated that any amount of xylitol may be used in the morsel composition as provided by the ranges above, without departing from the spirit or scope of the present disclosure.

Applicant has found that administering at least about 0.75 g of xylitol per dose through partaking of the morsel composition of the present disclosure may reduce MS levels, may reduce dental plaque, may suppress bacterial growth, and may reduce adhesiveness of plaque to thereby inhibit formation of, and reduce the incidence of, dental caries. It will be appreciated that in some instances it may be necessary to partake of at least one morsel composition, and in other instances it may be necessary to partake of more than one morsel composition to administer at least 0.075 g of xylitol in one dose, depending upon the size of the morsel composition.

It will be appreciated that as used herein the term "partaking" may be defined as eating, sucking, chewing, swallowing, ingesting, devouring, consuming, or masticating a morsel composition. Specifically, partaking of the xylitol morsel composition for at least five minutes after meals and snacks, when bacteria that causes dental caries is most active, may be advantageous for reducing MS levels and for maintaining and promoting oral health.

EXAMPLE 2

Xylitol Morsel Composition

| Xylitol Morsel Ingredients: | |
|---|---|
| xylitol | 0.48 g |
| natural flavors | 0.01 g |
| calcium stearate | 0.01 g |

In the case of the exemplary Xylitol Morsel of Example 2, the ingredients can be provided in the following proportions: xylitol—more than about 95%; natural flavors—more than about 2%; and calcium stearate—more than about 2%.

Another composition that may be present in the kit of the present disclosure may be a paste-like composition for brushing a user's teeth. It will be appreciated that the paste-like composition may be used as part of the kit or the paste-like composition may be used alone, as an individually packaged product, without departing from the scope of the present disclosure.

The paste-like composition of the present disclosure may comprise an effective amount of xylitol, water, silica, sorbitol, glycerin, at least one foaming agent, which may be sodium lauroyl sarcosinate or any other foaming agent that is currently known, or which may become known in the future, in the art, and at least one flavoring agent, for example mentha viridis (spearmint) leaf oil. The paste-like composition of the present disclosure may be characterized by the absence of fluoride. However, it will be appreciated that the composition of the paste may be modified to include, or used in conjunction with, fluoride without departing from the scope of the present disclosure.

It will be appreciated that the paste-like composition may comprise an amount of xylitol that may be present in a range from about 5% to about 50%, by weight, and more specifically in a range from about 15% to about 40%, by weight. For example, applicant has found that an amount of xylitol present in the paste-like composition of about 25%, by weight, to be advantageous. Additional ranges that may supply a desired amount of xylitol may include a range from about 20% to about 50% by weight; or a range from about 25% to about 40% by weight; or a range from about 30% to about 35% by weight. Other possible ranges that may supply a desired amount of xylitol may also include a range from about 5% to about 30% by weight; or a range from about 10% to about 25% by weight; or a range from about 15% to about 20% by weight. However, it will be appreciated that one of skill in the art may modify the present disclosure to include more or less than the above stated amount without departing from the scope of the present disclosure. It will be appreciated that any amount of xylitol may be used in the paste-like composition as provided in the ranges above, without departing from the spirit or scope of the present disclosure.

It will be appreciated that the paste-like composition may comprise more than about 20% water and silica, by weight. However, it will be appreciated that one of skill in the art may modify the present disclosure to include more or less than the above stated amount without departing from the scope of the present disclosure.

It will further be appreciated that the paste-like composition may comprise less than about 20% sorbitol, glycerin and sodium lauroyl sarcosinate, by weight. However, it will be appreciated that one of skill in the art may modify the present disclosure to include more or less than the above stated amount without departing from the scope of the present disclosure.

The paste-like composition of the present disclosure may further comprise the following ingredients: stevia, cellulose gum, carrageenan, calcium glycerophosphate, copper PCA, and zinc PCA, each of which may be present in less than about 1%, by weight.

Applicant has found that brushing a user's teeth with the paste-like composition of the present disclosure, which may comprise at least about 0.05 g to about 0.75 g of xylitol per dose, may be expected to reduce MS levels, reduce dental plaque, suppress bacterial growth, and may be expected to reduce adhesiveness of plaque to thereby inhibit formation of, and reduce the incidence of, dental caries. Specifically, brushing with the xylitol paste-like composition for at least one minute, sometime during the morning hours and sometime during the evening hours, or after partaking of the last meal and/or snack of the day, may be advantageous for reducing MS levels and for maintaining and promoting oral health.

EXAMPLE 3

Xylitol Paste-Like Composition

| Xylitol Paste Ingredients: | |
|---|---|
| water | 28% by weight |
| xylitol | 25% by weight |
| silica | 23% by weight |
| sorbitol | 13% by weight |
| glycerin | 05% by weight |
| sodium lauroyl sarcosinate | 03% by weight |
| mentha viridis (spearmint) leaf oil | 01% by weight |
| stevia | less than 01% by weight |
| cellulose gum | less than 01% by weight |
| carrageenan | less than 01% by weight |
| calcium glycerophosphate | less than 01% by weight |
| copper PCA | less than 01% by weight |
| zinc PCA | less than 01% by weight |

In the case of the exemplary Xylitol Paste of Example 3, the ingredients can be provided in the following proportions: water—greater than about 20%; silica—greater than about 20%; xylitol—about 20%; sorbitol—less than about 20%; glycerin—less than about 10%; sodium lauroyl sarcosinate—less than about 10%; mentha viridis (spearmint) leaf oil—less than about 3%; stevia—less than about 1%; cellulose gum—less than about 1%; carrageenan—less than about 1%; calcium glycerophosphate—less than about 1%; copper PCA—less than about 1%; and, zinc PCA—less than about 1%.

EXAMPLE 3A

Xylitol Paste-Like Composition

| Xylitol Paste Ingredients: | |
|---|---|
| water | 28% by weight |
| xylitol | 25% by weight |
| calcium phosphate | 23% by weight |
| sorbitol | 18% by weight |
| sodium lauroyl sarcosinate | 03% by weight |
| mentha viridis (spearmint) leaf oil | 01% by weight |
| stevia | less than 01% by weight |
| carrageenan | less than 01% by weight |
| calcium glycerophosphate | less than 01% by weight |
| copper PCA | less than 01% by weight |
| zinc PCA | less than 01% by weight |

In the case of the exemplary Xylitol Paste of Example 3A, the ingredients can be provided in the following proportions: water—greater than about 20%; calcium phosphate—greater than about 20%; xylitol—about 20%; sorbitol—less than about 20%; sodium lauroyl sarcosinate—less than about 10%; mentha viridis (spearmint) leaf oil—less than about 3%; stevia—less than about 1%; carrageenan—less than about 1%; calcium glycerophosphate—less than about 1%; copper PCA—less than about 1%; and, zinc PCA—less than about 1%.

Another composition that may be present in the kit of the present disclosure may be an oral rinse composition that may be used after brushing the user's teeth. It will be appreciated that the oral rinse composition may be used as part of the kit or the oral rinse composition may be used alone, as an individually packaged product, without departing from the scope of the present disclosure.

The oral rinse composition of the present disclosure may comprise an effective amount of xylitol, water, glycerin, at least one flavoring agent, and sorbitol. The oral rinse composition of the present disclosure may be characterized by the absence of fluoride. However, it will be appreciated that the composition of the oral rinse may be modified to include, or may be used in conjunction with, fluoride without departing from the scope of the present disclosure.

It will be appreciated that the oral rinse composition may comprise more than about 20% water, by weight. More specifically, water may present in the oral rinse composition in a range from about 20% to about 80%, by weight. Other possible ranges include a range from about 50% to about 80% by weight; or a range from about 60% to about 75% by weight; or a range from about 65% to about 70% by weight. Additional ranges may also include a range from about 20% to about 50% by weight; or a range from about 25% to about 45% by weight; or about 30% to about 35% by weight. However, it will be appreciated that one of skill in the art may modify the present disclosure to include more or less than the above stated amount without departing from the scope of the present disclosure.

It will be appreciated that the oral rinse composition may comprise an amount of xylitol that may be present in a range from about 5% to about 60%, by weight, and more specifically in a range from about 15% to about 50%, by weight. For example, applicant has found that including about 25% by weight of xylitol in the oral rinse composition to be an advantageous amount of xylitol. Additional ranges that may supply a desired amount of xylitol may include a range from about 40% to about 60% by weight; or a range from about 45% to about 65% by weight; or a range from about 50% to about 65% by weight. Other possible ranges that may supply a desired amount of xylitol may also include a range from about 5% to about 40% by weight; or a range from about 15% to about 30% by weight; or a range from about 20% to about 25% by weight. However, it will be appreciated that one of skill in the art may modify the present disclosure to include more or less than the above stated amounts without departing from the scope of the present disclosure. It will be appreciated that any amount of xylitol may be used in the oral rinse composition as provided by the ranges above, without departing from the spirit or scope of the present disclosure.

Additionally, the oral rinse composition may comprise less than about 20% glycerin, by weight, specifically glycerin may be present in the oral rinse composition in a range from about 5% to about 20%, by weight. Other possible ranges may include a range from about 3% to about 10% by weight; or a range from about 5% to about 8% by weight. Additional ranges may also include a range from about 10% to about 20% by weight; or a range from about 12% to about 18% by weight; or about 15% to about 17% by weight. However, it will be appreciated that one of skill in the art may modify the present disclosure to include more or less than the above stated amount without departing from the scope of the present disclosure. The oral rinse composition may further comprise polysorbate 20, mentha viridis leaf oil, sodium benzoate, menthol, citric acid, zinc PCA, and ascorbic acid, which may be present in the oral rinse composition in less than about 1%, by weight.

Applicant has found that rinsing a user's teeth and oral cavity with the oral rinse composition of the present disclosure, which may comprise at least about 0.75 g of xylitol per dose, may be expected to reduce MS levels, expected to reduce dental plaque, may be expected to suppress bacterial growth, and may also be expected to reduce adhesiveness of plaque to thereby inhibit formation of, and reduce the incidence of, dental caries. Specifically, rinsing with the xylitol oral rinse composition for at least one minute after brushing, and at least in the evening, may be advantageous for reducing MS levels and for maintaining and promoting oral health.

EXAMPLE 4

Xylitol Oral Rinse Composition

| Xylitol Oral Rinse Ingredients: | |
| --- | --- |
| water | 68% by weight |
| xylitol | 25% by weight |
| glycerin | 05% by weight |
| sorbitol | 01% by weight |
| polysorbate 20 | less than 01% by weight |
| mentha viridis leaf oil | less than 01% by weight |
| sodium benzoate | less than 01% by weight |
| menthol | less than 01% by weight |
| citric acid | less than 01% by weight |
| zinc PCA | less than 01% by weight |
| ascorbic acid | less than 01% by weight |

In the case of the exemplary Xylitol Oral Rinse of Example 4, the ingredients can be provided in the following proportions: water—greater than about 50%; xylitol—greater than about 20%; glycerin—less than about 10%; sorbitol—less than about 3%; polysorbate 20—less than about 1%; mentha viridis leaf oil—less than about 1%; sodium benzoate—less than about 1%; menthol—less than about 1%; citric acid—less than about 1%; zinc PCA—less than about 1%; and, ascorbic acid—less than about 1%.

EXAMPLE 4A

Xylitol Oral Rinse Composition

| Xylitol Oral Rinse Ingredients: | |
| --- | --- |
| water | 68% by weight |
| xylitol | 25% by weight |
| glycerin | 05% by weight |
| sorbitol | 01% by weight |
| PEG-40 hydrogenated castor oil | less than 01% by weight |
| mentha viridis leaf oil | less than 01% by weight |
| potassium sorbate | less than 01% by weight |
| menthol | less than 01% by weight |
| malic acid | less than 01% by weight |
| zinc PCA | less than 01% by weight |
| ascorbic acid | less than 01% by weight |

In the case of the exemplary Xylitol Oral Rinse of Example 4A, the ingredients can be provided in the following proportions: water—greater than about 50%; xylitol—greater than about 20%; glycerin—less than about 10%; sorbitol—less than about 3%; PEG-40 hydrogenated castor oil—less than about 1%; mentha viridis leaf oil—less than about 1%; potassium sorbate—less than about 1%; menthol—less than about 1%; malic acid—less than about 1%; zinc PCA—less than about 1%; and, ascorbic acid—less than about 1%.

It should be noted that other ingredients could be used in the compositions of either Example 4 or Example 4A instead of sodium benzoate as illustrated above without departing from the spirit or scope of the present disclosure. For example, sodium benzoate could be replaced with potassium sorbate, benzoate potassium, or benzoic acid without departing from the spirit or scope of the present disclosure.

It should further be noted that other ingredients could be used in Example 4 or Example 4A instead of citric acid as illustrated above without departing from the spirit or scope of the present disclosure. For example, citric acid could be replaced with malic acid or tartaric acid without departing from the spirit or scope of the present disclosure.

Likewise, it should be noted that other ingredients having similar characteristics and properties as the above-identified exemplary ingredients in the chewing gum composition, the morsel composition, the paste-like composition, and the oral rinse composition may be used and substituted in the present disclosure, without departing from the spirit or scope of the present disclosure.

Figure 3:
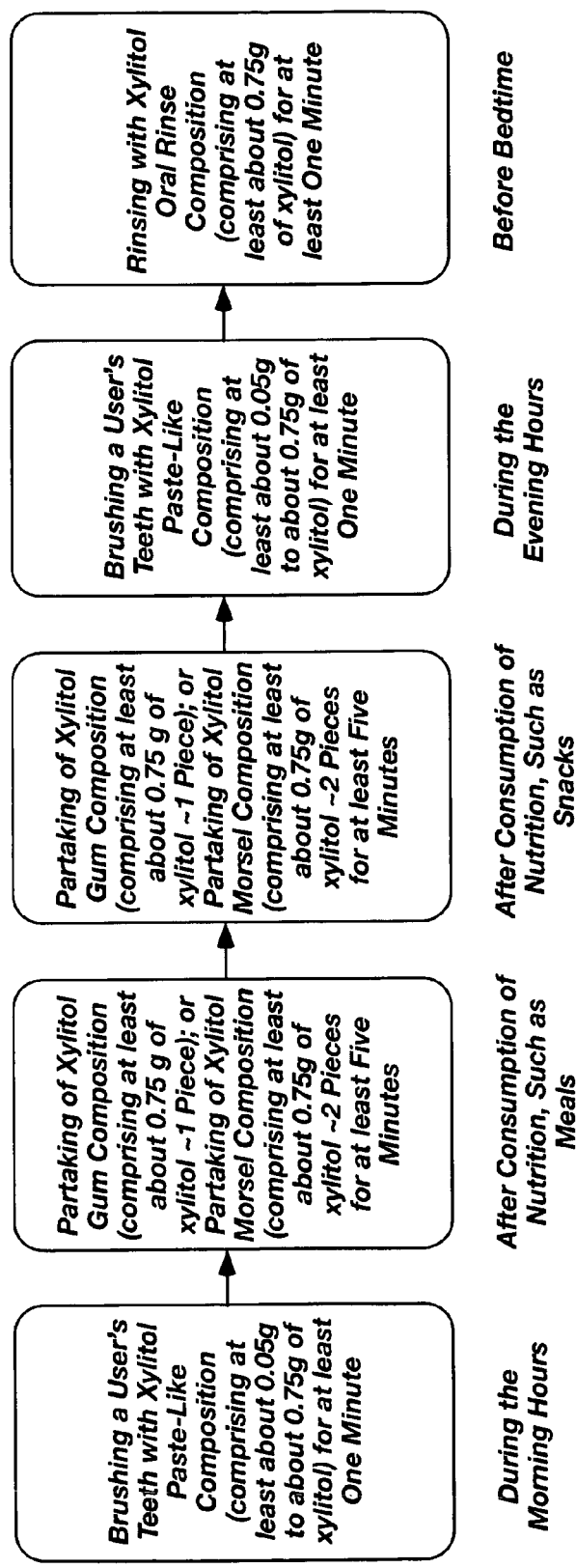
FIG. 3 is a flow chart illustrating an exemplary method of promoting oral hygiene and to reduce dental plaque, suppress bacterial growth, and reduce adhesiveness of plaque in a user's oral cavity to thereby inhibit formation of dental caries in accordance with the teachings and principles of the present disclosure.

Referring now to FIGS. 3-6, which illustrate exemplary methods of using the compositions described in detail above. More specifically, FIG. 3 illustrates a method for promoting oral hygiene and to reduce dental plaque, suppress bacterial growth, and reduce adhesiveness of plaque in a user's oral cavity to thereby inhibit formation of dental caries. The steps illustrated in FIG. 3 include the following. First, during the morning hours of the day a user may brush his or her teeth using the xylitol paste-like composition, which may advantageously comprise at least about 0.05 g to about 0.75 g of xylitol per dose or per use. Applicant has found that brushing with the xylitol paste-like composition for at least one minute allows the xylitol present in the paste-like composition to provide its beneficial effects.

The second and third steps of the method include the user partaking of the xylitol gum composition, which may advantageously comprise at least about 0.75 g of xylitol in one piece of the gum composition, after consumption of nutrition, such as meals or snacks when tooth brushing is not as convenient or readily available. Alternatively, the user may select to partake of the xylitol morsel, which may advantageously comprise at least about 0.75 g of xylitol in one or more pieces of the morsel composition, instead of, or in addition to, partaking of the chewing gum composition. Applicant has found that partaking of the xylitol chewing gum or morsel compositions, or any combination thereof, for at least five minutes allows the xylitol present in those compositions to provide its beneficial effects.

The fourth and fifth steps of the method illustrated in FIG. 3 may be grouped together for convenience of the user, although such is not required. The fourth step of the method includes the user brushing his or her teeth using the xylitol paste-like composition, which may advantageously comprise at least about 0.05 g to about 0.75 g of xylitol per dose or per use, during the evening hours. Typically, this step will be after the last meal or snack of the day and just prior to bedtime. Thereafter, the fifth step of the method may be completed. The fifth step of the method includes rinsing the user's teeth and oral cavity with the oral rinse composition, which may advantageously comprise at least about 0.75 g of xylitol per dose or per use, before bedtime. Applicant has found that brushing with the xylitol paste-like composition for at least one minute; and rinsing the user's teeth and oral cavity with the xylitol oral rinse composition for at least one minute allows the xylitol present in the paste-like and oral rinse compositions to provide its beneficial effects.

Figure 4:
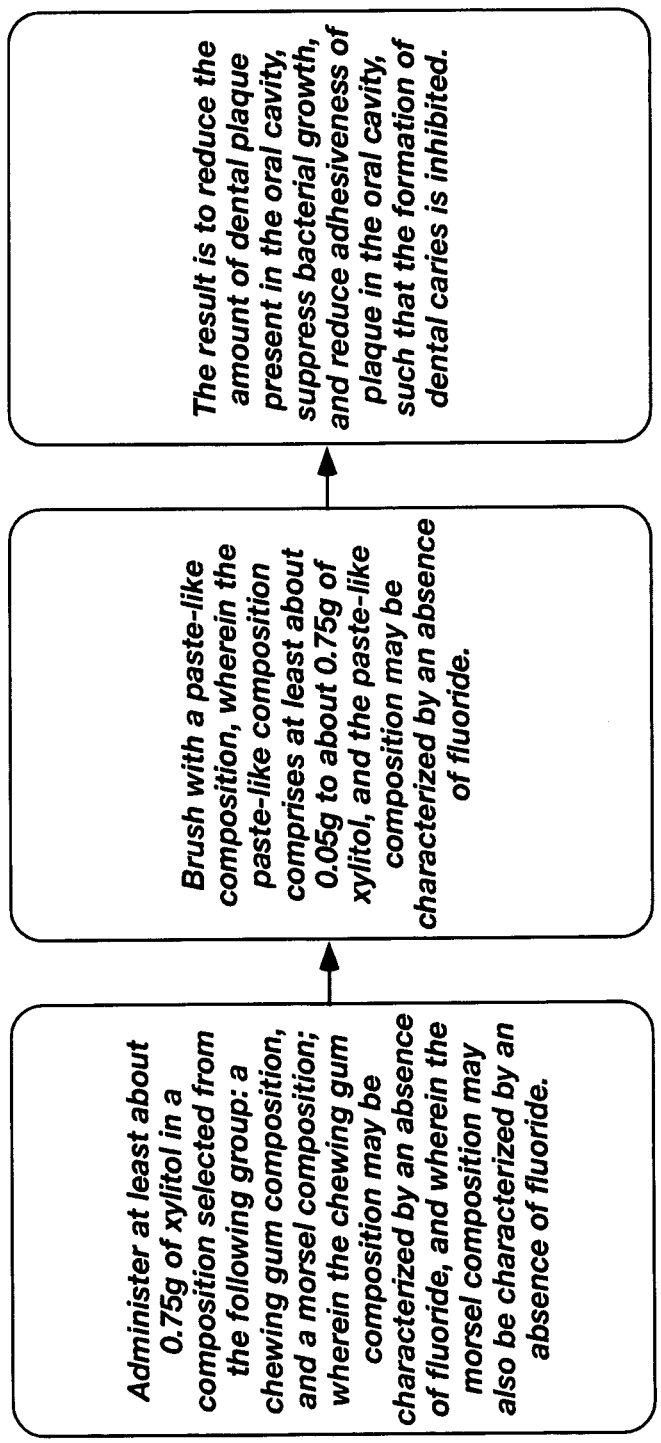
FIG. 4 is another flow chart illustrating an exemplary method of promoting oral hygiene and to reduce dental plaque, suppress bacterial growth, and reduce adhesiveness of plaque in a user's oral cavity to thereby inhibit formation of dental caries in accordance with the teachings and principles of the present disclosure.
Figure 5:
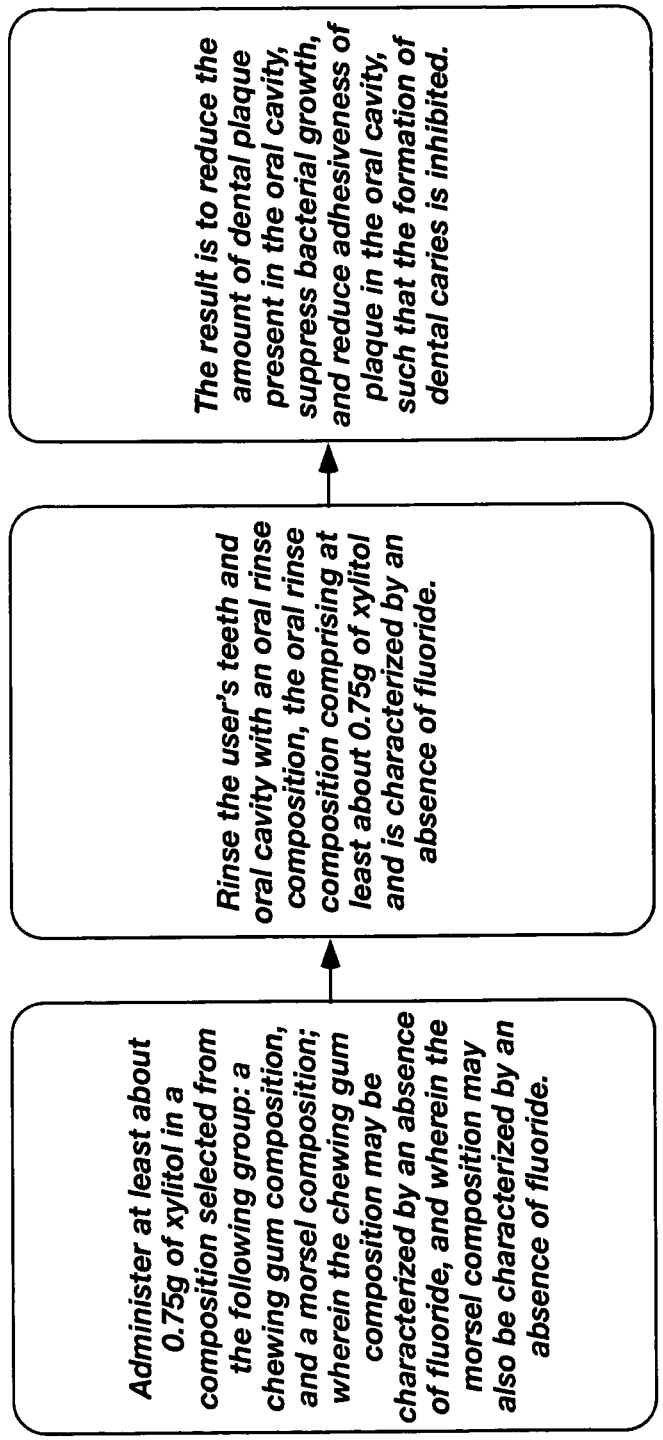
FIG. 5 is still another flow chart illustrating an exemplary method of promoting oral hygiene and to reduce dental plaque, suppress bacterial growth, and reduce adhesiveness of plaque in a user's oral cavity to thereby inhibit formation of dental caries in accordance with the teachings and principles of the present disclosure.
Figure 6:
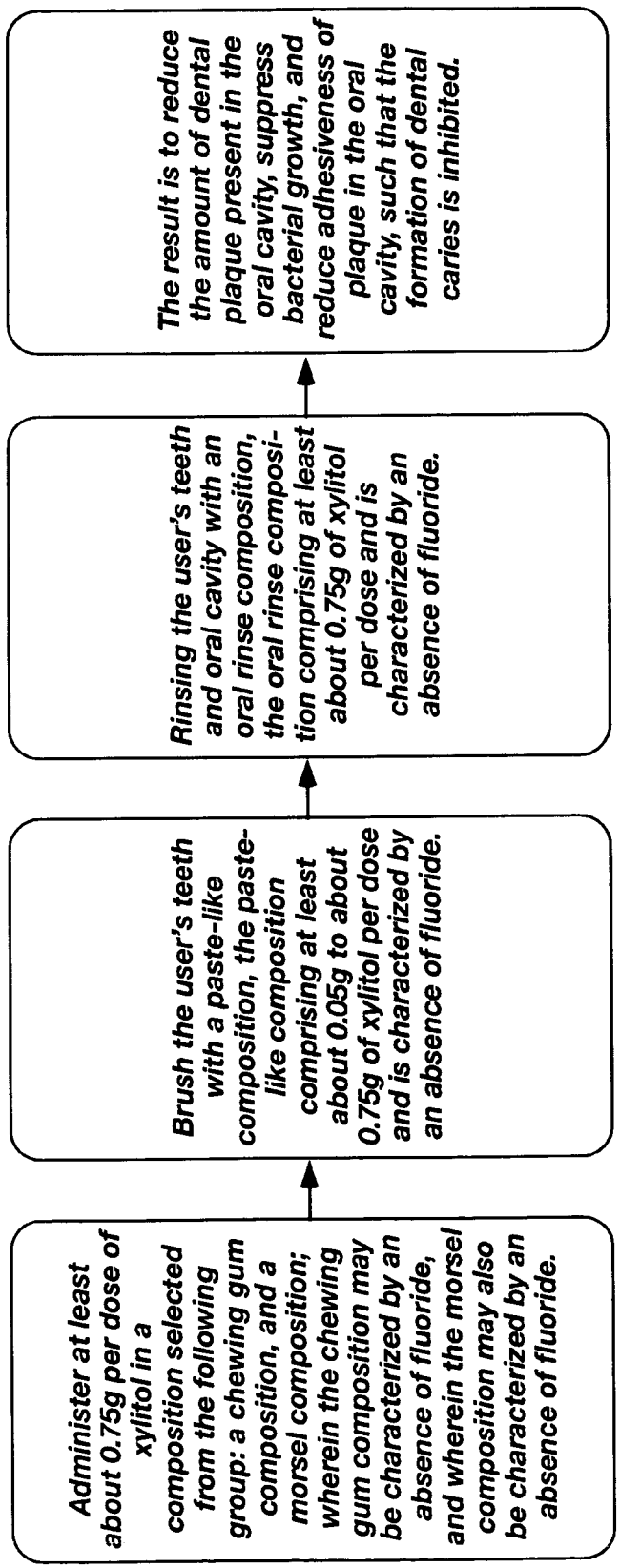
FIG. 6 is yet another flow chart illustrating an exemplary method of promoting oral hygiene and to reduce dental plaque, suppress bacterial growth, and reduce adhesiveness of plaque in a user's oral cavity to thereby inhibit formation of dental caries in accordance with the teachings and principles of the present disclosure.

It will be appreciated that there may be other methods that may be used without departing from the spirit and scope of the present disclosure. For example, a combination of the above enumerated steps comprising more or less than the above referenced steps may be beneficial, as long as the effective amount of xylitol may be supplied to the user's teeth and oral cavity. FIGS. 4-6 illustrate such examples, but it should be noted that there may be other combinations that may also be utilized without departing from the scope of the present invention.

FIG. 4 illustrates another exemplary method for promoting oral hygiene and to reduce dental plaque, suppress bacterial growth, and reduce adhesiveness of plaque in a user's oral cavity to thereby inhibit formation of dental caries is illustrated. The steps of the method illustrated in FIG. 4 may comprise, first, administering at least about 0.75 g of xylitol in either a chewing gum composition or a morsel composition to a user, wherein both the chewing gum composition and the morsel composition may be characterized by an absence of fluoride. Second, brushing the user's teeth with a paste-like composition, wherein the paste-like composition may comprise at least about 0.05 g to about 0.75 g of xylitol, and may be characterized by an absence of fluoride. Following the above steps may reduce dental plaque, suppress bacterial growth, and reduce adhesiveness of plaque, such that the formation of dental caries is inhibited.

Referring now to FIG. 5, wherein another exemplary method for promoting oral hygiene and to reduce dental plaque, suppress bacterial growth, and reduce adhesiveness of plaque in a user's oral cavity to thereby inhibit formation of dental caries is illustrated. The steps of the method illustrated in FIG. 5 may comprise, first, administering at least about 0.75 g of xylitol in either a chewing gum composition or a morsel composition, wherein both the chewing gum composition and the morsel composition may be characterized by an absence of fluoride. Second, rinsing the user's teeth and oral cavity with an oral rinse composition that may comprise at least about 0.75 g of xylitol and may be characterized by an absence of fluoride. Following the above steps may reduce dental plaque, suppress bacterial growth, and reduce adhesiveness of plaque to thereby inhibit formation of dental caries.

Referring now to FIG. 6, another method for promoting oral hygiene and to reduce dental plaque, suppress bacterial growth, and reduce adhesiveness of plaque in a user's oral cavity to thereby inhibit formation of dental caries is illustrated. The steps of the method may include, first, administering at least about 0.75 g of xylitol in either a chewing gum composition or a morsel composition to a user, wherein both the chewing gum composition and the morsel composition may be characterized by an absence of fluoride. Second, brushing the user's teeth with a paste-like composition, wherein the paste-like composition may comprise at least about 0.05 g to about 0.75 g of xylitol, and may be characterized by an absence of fluoride. Last, rinsing the user's teeth and oral cavity with an oral rinse composition that may comprise at least about 0.75 g of xylitol and may be characterized by an absence of fluoride. Following the above steps may reduce dental plaque, suppress bacterial growth, and reduce adhesiveness of plaque to thereby inhibit formation of dental caries.

In accordance with the features and combinations described above, a useful regimen or method for promoting oral hygiene and to reduce dental plaque, suppress bacterial growth, and reduce adhesiveness of plaque in a user's oral cavity to thereby inhibit formation of dental caries, may include the steps of:

(a) brushing a user's teeth with a paste-like composition during morning hours, the paste-like composition comprising an amount of xylitol between a range of about 0.05 g to about 0.75 g and is characterized by an absence of fluoride;

(b) administering at least about 0.75 g of xylitol after meals or snacks in a composition selected from the group consisting of: a chewing gum composition, and a morsel composition, wherein the chewing gum composition is characterized by an absence of fluoride, and wherein the morsel composition is characterized by an absence of fluoride;

(c) brushing the user's teeth with the paste-like composition during evening hours; and (d) rinsing the user's oral cavity with an oral rinse comprising at least about 0.75 g of xylitol before bedtime, to reduce dental plaque, suppress bacterial growth, and reduce adhesiveness of plaque to thereby inhibit formation of dental caries.

It will be appreciated that other products and compositions may be utilized in accordance with the present disclosure, including: xylitol-coated floss, cavity protection gel for infants and toddlers who are teething, a xylitol tooth varnish, a xylitol hard candy, a xylitol gummy bear and other xylitol confectionary products.

Those having ordinary skill in the relevant art will appreciate the advantages provided by the features of the present disclosure. For example, it is a potential feature of the present disclosure to provide a kit for promoting oral health and hygiene that is simple to use, and that may comprise a chewing gum composition, a morsel composition, a paste-like composition, and an oral rinse composition. Another potential feature of the present disclosure is to provide such a kit for promoting oral health and hygiene, wherein each of the compositions of the kit comprises effective amounts of xylitol.

It is a further potential feature of the present disclosure to provide the components of the kit for promoting oral health and hygiene individually, such that an amount of a single composition may be purchased individually without each of the other compositions. For example, a xylitol chewing gum composition, a xylitol morsel composition, i.e. mints, lozenges and candies, a xylitol paste-like composition, a xylitol oral rinse composition, as well as other oral products containing xylitol may be provided for individual distribution, i.e., through retail or wholesale outlets. It is yet another potential feature of the present disclosure to provide fluoride-free products. It is another potential feature to promote oral health and hygiene through use of a kit that may comprise products that are appetizing and that reduce dental plaque, suppress bacterial growth, and reduce adhesiveness of plaque to thereby inhibit formation of dental caries.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description by this reference, with each claim standing on its own as a separate embodiment of the present disclosure.

It is to be understood that the above-described compositions and arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been described above with particularity and detail, it will be apparent to those of ordinary skill in the art that numerous modifications, including, but not limited to, variations in amounts, ingredients, compositions, configurations, process steps, materials, form, function and manner of use, may be made without departing from the principles and concepts set forth herein.

What is claimed is:

1. A method for promoting oral hygiene by administering a sufficiently large amount of xylitol during a single day to operate as an antimicrobial agent for reducing dental plaque, suppressing bacterial growth and reducing adhesiveness of plaque in a user's oral cavity to thereby inhibit formation of dental caries, consisting of:

administering a total of about 6 grams to about 10 grams of xylitol during a single day to a user in increments throughout the day, wherein the about 6 grams to about 10 grams of xylitol is administered to the user in the following compositions:

a chewing gum composition consisting of xylitol, gum base, natural flavors, glycerin, gum arabic, lecithin, titanium dioxide, carnauba wax, and confectioner's glaze;

wherein the chewing gum composition is chewed by the user after consumption of nutrition or at other intervals during a single day;

wherein xylitol is present in the chewing gum composition in an amount of at least 0.75 grams per piece, such that a total of about 4 grams to about 8 grams of xylitol is administered to the user in a single day through the chewing gum composition; and an oral rinse composition consisting of water, xylitol, glycerin, polysorbate 20, natural flavors, sodium benzoate, menthol, citric acid, zinc PCA, and ascorbic acid;

wherein xylitol is present in the oral rinse composition in an amount of about 25% to about 50% by weight, such that the user ingests about 1 gram to about 2 grams of xylitol in a single day using the oral rinse composition;

such that about 6 grams to about 10 grams of xylitol is incrementally administered to the user throughout a single day, thereby operating as an antimicrobial agent to reduce dental plaque, suppress bacterial growth, and reduce adhesiveness of plaque to thereby inhibit formation of dental caries.

* * * * *